United States Patent [19]
Craft

[11] Patent Number: 5,301,699
[45] Date of Patent: Apr. 12, 1994

[54] DENTAL FLOSS DISPENSER APPARATUS

[76] Inventor: Thomas Craft, 1809 Warwick Ave., 15 NW., Warwick, R.I. 02889

[21] Appl. No.: 989,779

[22] Filed: Dec. 14, 1992

[51] Int. Cl.5 .................................. A61C 15/00
[52] U.S. Cl. ..................... 132/325; 132/326
[58] Field of Search ............... 132/323, 324, 325, 326, 132/327

[56] References Cited

U.S. PATENT DOCUMENTS

| | | |
|---|---|---|
| 844,181 | 2/1907 | Overbaugh . |
| 1,102,401 | 7/1914 | Gamble ................ 132/325 |
| 1,582,000 | 4/1926 | Gesell ................. 132/326 |
| 1,588,307 | 6/1926 | Cammack . |
| 1,723,842 | 8/1929 | Cammack . |
| 2,577,597 | 12/1951 | Wright et al. ......... 132/326 |
| 2,742,047 | 4/1956 | Ness ................. 132/326 |
| 2,756,758 | 7/1956 | Segerblom ............ 132/326 |
| 3,327,719 | 6/1967 | Ford ................. 132/326 |
| 3,340,881 | 12/1967 | Cowan ................ 132/92 |
| 3,759,273 | 9/1973 | Knaus ................ 132/326 |
| 3,871,393 | 3/1975 | Wharton .............. 132/325 |
| 3,903,907 | 9/1975 | Knaus ................ 132/326 |
| 4,495,957 | 1/1985 | Beggs et al. .......... 132/92 A |
| 4,508,125 | 4/1985 | Loubier .............. 132/326 |
| 4,574,823 | 3/1986 | Uriss ................. 132/325 |
| 4,637,412 | 1/1987 | Martinez ............. 132/323 |
| 4,655,234 | 4/1987 | Bowden ............... 132/325 |
| 4,660,584 | 4/1987 | Wofford .............. 132/325 |
| 4,901,742 | 2/1990 | Olson ................ 132/325 |
| 4,920,993 | 5/1990 | Mackie ............... 132/324 |
| 5,052,420 | 10/1991 | Chen ................. 132/325 |

FOREIGN PATENT DOCUMENTS 0477739 10/1951 Canada ................. 132/325

Primary Examiner—Gene Mancene
Assistant Examiner—Frank A. LaViola
Attorney, Agent, or Firm—Barlow & Barlow, Ltd.

[57] ABSTRACT

A dental floss dispenser is shown having two mirror image housing halves formed with a main body portion capturing a spool of floss and an arcuately extending arm with floss guided from the spool through a locking station out of the housing to the free end of the arm and back into the housing along the arm and back through the locking station and out of the housing. A severing blade is provided to sever used portions of floss or selected lengths of fresh floss from the spool.

12 Claims, 4 Drawing Sheets

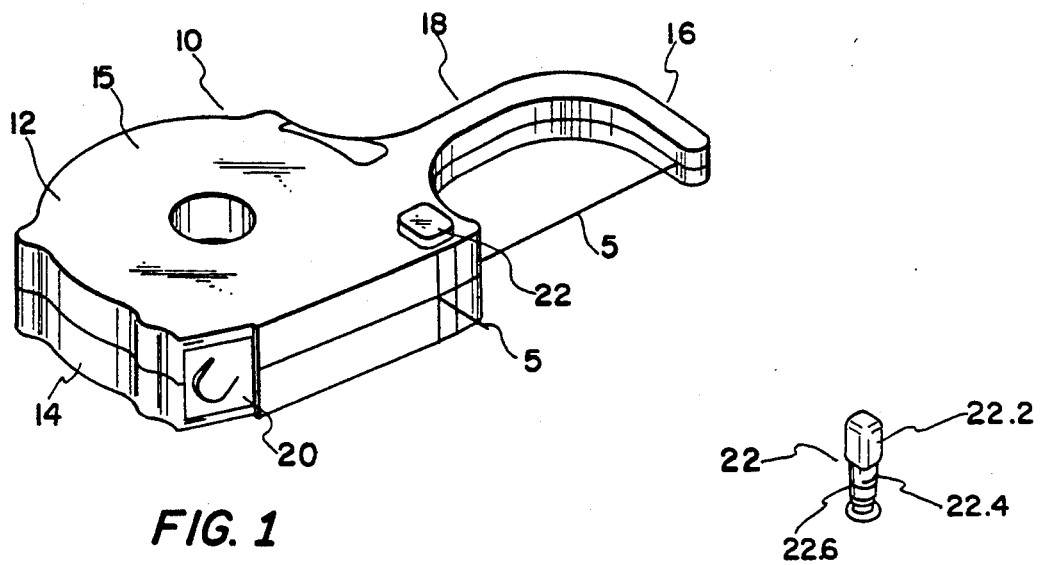
FIG. 1
FIG. 1B
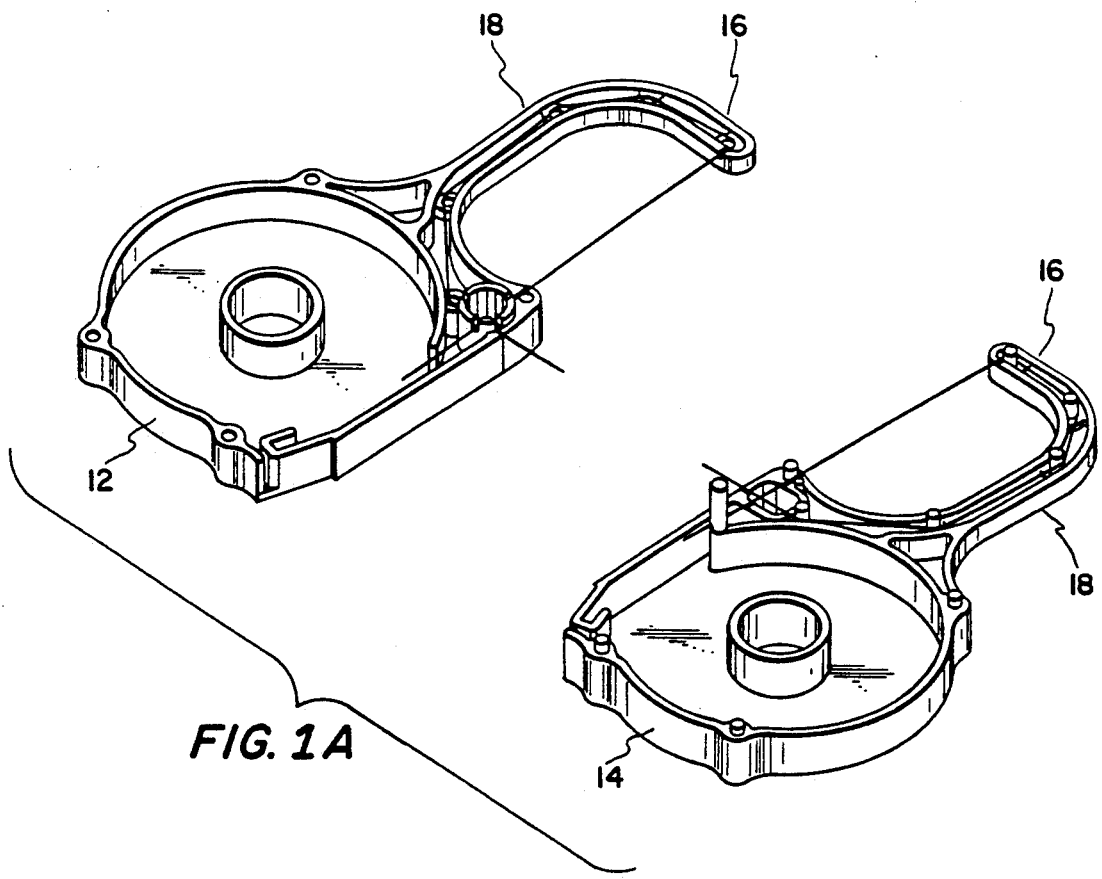
FIG. 1A

DENTAL FLOSS DISPENSER APPARATUS

This invention relates generally to apparatus for facilitating the cleaning of teeth and more specifically, to a dispenser for dental floss and for aiding in the flossing of teeth.

Dentists have, for many years, advocated the regular use of floss to clean one's teeth by removing plaque and food particles which, if left on the surface of the teeth, can lead to serious injury to gum tissue. The process of flossing one's teeth, however, is tedious and for those who have any problems of dexterity, very difficult to perform in the conventional manner of taking a long length of a strand of floss and wrapping it around one's fingers and trying to maneuver a taught portion in between contiguous teeth, particularly in the posterior of the mouth. Further, the process is unpleasant in that the used portion of the floss is continuously passed through one's fingers in a constant attempt to present fresh portions going from one tooth to another. As a result, many people fail to floss their teeth on a regular basis. Further, when they do floss their teeth, they end up wasting a significant percentage of the floss since so much length is required merely to hold on to the strand.

Although the prior art is replete with various devices to help in the task of teeth flossing, they are unsatisfactory for various reasons, generally because they are relatively complex and expensive. That is, such devices typically employ a number of moving parts including ratchet and pawl mechanisms, intermeshing gears, spring tension means, clutches, brakes and the like.

It is an object of the present invention to provide a dental floss dispenser and flossing aid which is simple in construction, reliable and easy to use. Another object of the invention is the provision of a dental floss dispenser which can be used either to dispense a fresh length of floss strand of any selected length, or to provide a taught length which can easily be manipulated between a user's teeth.

SUMMARY OF THE INVENTION

Briefly, in accordance with the invention, first and second, preferably molded, housing halves have a main body portion which entraps a spool of dental floss and an arcuately extending arm. Guide means form a path for a first portion of a strand of floss to extend from the spool through a locking station out of the housing to the distal free end of the arm and back into the housing and a second portion to extend along a series of pegs formed in the arm back through the locking station and then out of the housing along a side of the housing where a severing means is disposed. According to a feature of the invention, the locking station comprises a locking pin axially moveable between an unlocked position with a frusto-conical surface portion of a pin loosely received in a complimentary shaped frusto-conical seat surface portion and a locked position with the frusto-conical surface portion of the pin closely received in the frusto-conical surface portion of the seat. The pin is formed with first and second slots axially spaced along the frusto-conical surface portion of the pin. The first portion of the floss strand is trained through one slot and the second portion of the floss strand is trained through the second slot. When the pin is in the locked position, both the first and second portions of the strand are brought into tightly held frictional engagement between the frusto-conical surface portions providing a tensioned loop from the locking station out of the housing, over to the outer portion of the arm around the arcuate arm, and back to the locking station. When the locking pin is in the unlocked position, the frusto-conical surface of the pin is loosely received in the frusto-conical surface portion of the seat with the floss strand free to move through the locking station when pulled. According to another feature of the invention, the locking pin is provided with anti-rotation means to maintain the pin in a selected angular orientation so that the slots are aligned with the intended floss path.

BRIEF DESCRIPTION OF THE DRAWINGS

FIG. 1 is a perspective view of a floss dispenser made in accordance with the invention;

FIG. 1a is a perspective view of the top and bottom detached housing halves used in the FIG. 1 dispenser apparatus;

FIG. 1b is a perspective view of a locking pin used in the FIG. 1 dispenser apparatus;

As seen in FIG. 1, a dental floss dispenser 10 is shown comprising top and bottom housing halves 12, 14 respectively, which, as will be described in detail below, interfit and snap together to capture in a main body portion 15, a supply of dental floss, a strand S of which is guided along a path so that it extends from the supply out of the housing to a distal free end portion 16 of an arcuately shaped arm 18 back into the main body portion 15 of the housing and then back out of the housing so that the free end of strand S can be severed by severing means 20 as desired. A pin 22 is axially moveable between a depressed, locked position in which a first portion of strand S passing through a locking station, to be described below, out along arm 18 and a second portion of strand S passing back through the locking station from arm 18 are tightly held or locked and a second raised (as seen in FIG. 1), or unlocked position in which the strand can be pulled out from a floss supply. Preferably, housing halves 12 and 14 are formed of suitable moldable synthetic resin.

Figures 2, 3:
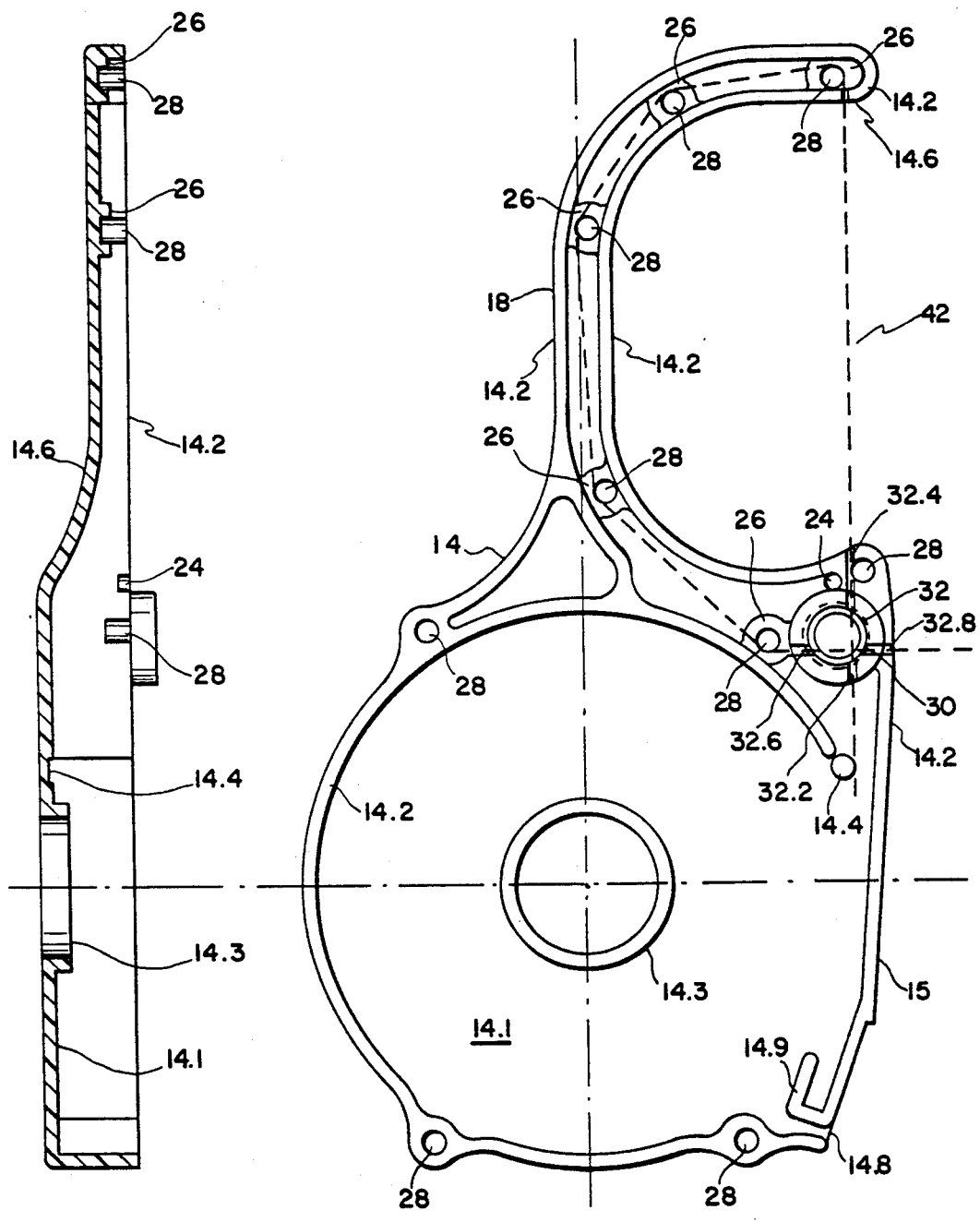
FIG. 2 is a plan view of one housing half.
FIG. 3 is a sectional view taken through FIG. 2 showing details of floss path defining and interconnecting pegs as well as the locking pin seats.

With particular reference to FIGS. 2 and 3, first housing half 14 has a bottom wall 14.1 with an outer side wall section 14.2 and an inner side wall portion 14.4 to define a main body portion 15 which serves as a dental floss supply section particularly adapted to receive a spool of floss.

Side wall 14.2 is adapted to provide a first height, along with a corresponding side wall of housing half 12 to be discussed below, suitable to receive a standard floss spool. Bottom wall 14.1 is displaced inwardly as noted at 14.6 in FIG. 3, to a reduced height for arm 18. Arm 18 extends arcuately from main body portion 15 to free end portion 16 and has a plurality of upstanding pegs 24 extending from reinforcing boss areas 26 having a top surface spaced below the top surface of side wall 14.2.

Pegs 28, similar to pegs 24, are spaced about main body portion 15 but extend upwardly from the top surface of wall 14.2.

A locking station 30 (see also FIG. 6–9) comprises a hub 32 having an inner surface portion 34 generally configured as a frusto-conical surface with the smaller diameters being adjacent bottom wall 14.1 and the larger diameters being adjacent top wall 14.2. An annular ridge 36 projects into an opening 38 formed in bottom wall 14.1 adapted to receive a locking pin 22 therethrough.

Figure 8:
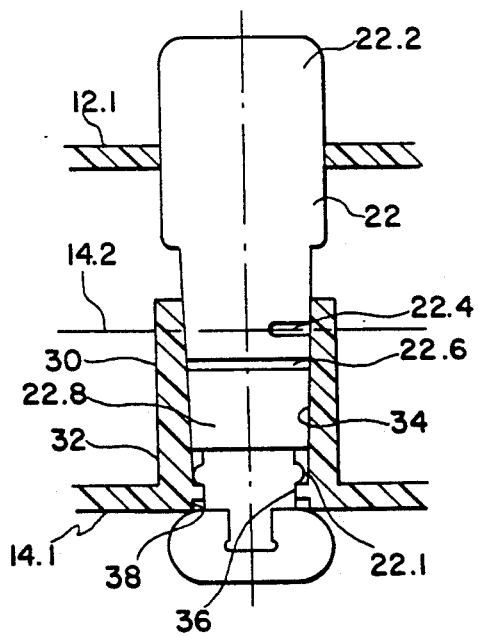
FIG. 8 is a sectional view taken through the locking pin seat shown with the locking pin in the unlocked position.
Figure 9:
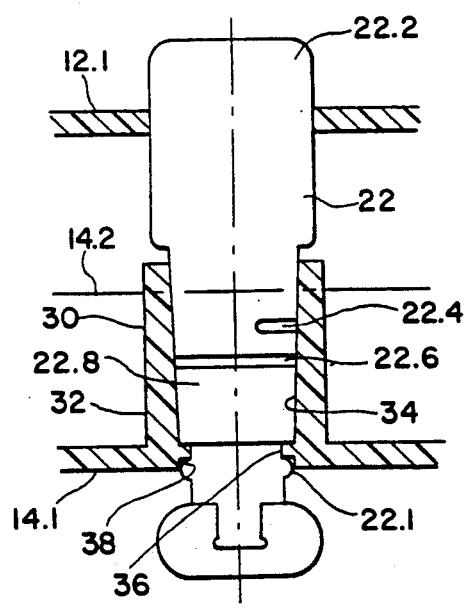
FIG. 9 is a sectional view similar to FIG. 8 but showing the locking pin in the locked position.

Locking pin 22, seen in FIGS. 8 and 9, has a first generally rectangular portion 22.2 received in a complimentary rectangular opening in wall portion 12.1 of the second housing half 12 to be described below which provides an anti-rotation feature for pin 22 maintaining a selected angular orientation of the pin so that a pair of slots 22.4, 22.6 spaced along the longitudinal axis in a portion 22.8 intermediate the ends of the pin are maintained in selected angular orientations. Slots 22.4 and 22.6 are each formed with opposed side walls lying in planes which are perpendicular to the longitudinal axis of pin 22. Slot 22.4 has a bottom surface which is aligned with grooves 32.2 and 32.4 formed in the top of hub 32 while slot 22.6 has a bottom surface aligned with grooves 32.6 and 32.8 also formed in the top of hub 32, the two bottom surfaces extending in directions generally perpendicular with one another. Intermediate portion 22.8 is formed with a surface which is generally frusto-conical having its larger diameters adjacent top wall 14.2 and its smaller diameters adjacent bottom wall 14.1. The frusto-conical surface portion 22.8 of pin 22 and inner surface portion 34 of hub 32 are formed so that they closely match one another. A protrusion 22.10, preferably annual in configuration, is formed on the end portion of pin 22 opposite end 22.2. Pin 22 is axially moveable from the unlocked or upper position shown in FIG. 8 with protrusion 22.10 above ridge 36 and with surface portions 22.8 being loosely received within surface portion 34 to the locked position shown in FIG. 9 with protrusion 22.10 forced below ridge 36 and with surface portion 22.8 tightly received in surface portion 34.

Figures 4, 5:
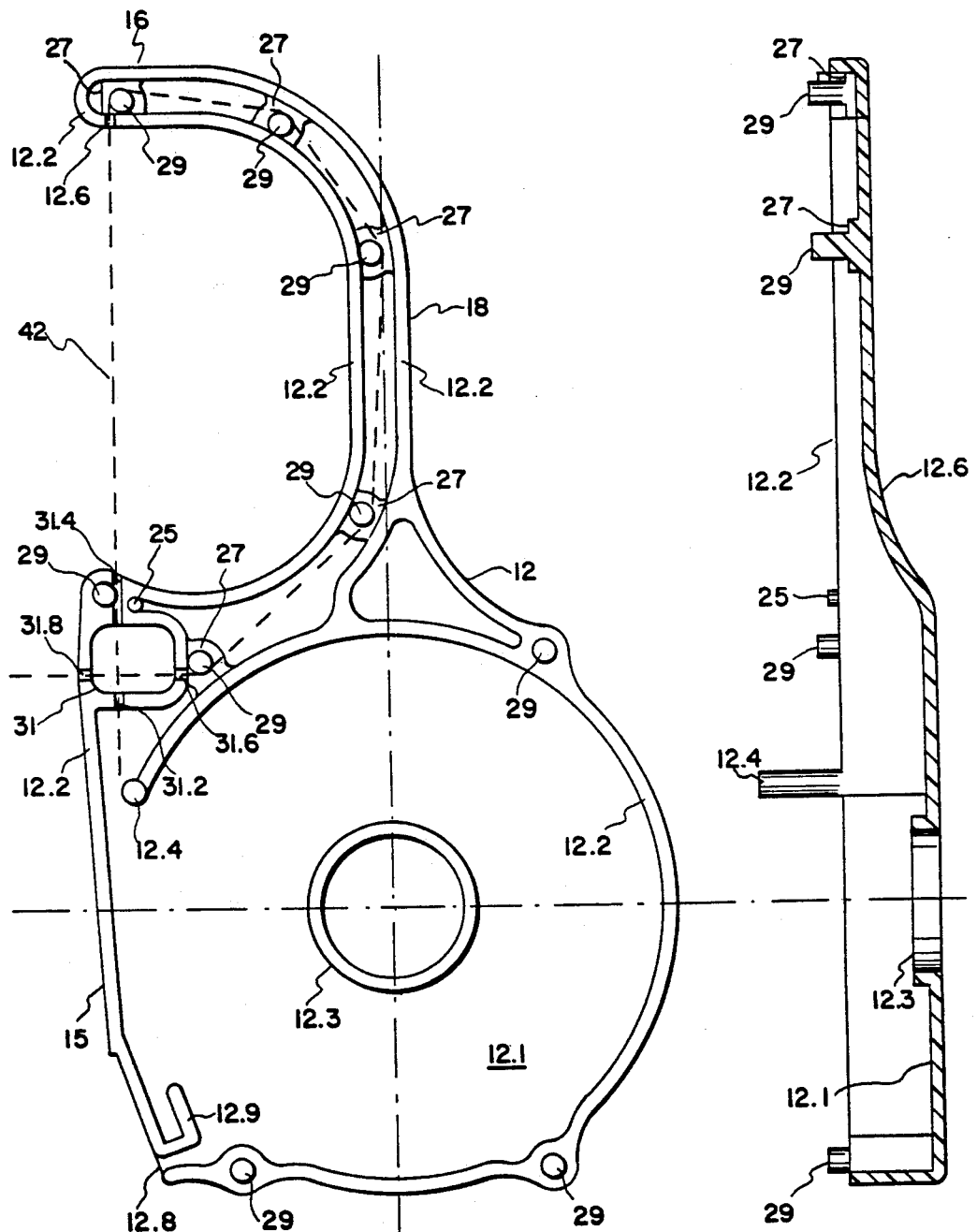
FIG. 4 is a plan view of a second housing half.
FIG. 5 is a sectional view taken through FIG. 4 showing details of the peg receiving apertures.
Figure 6:
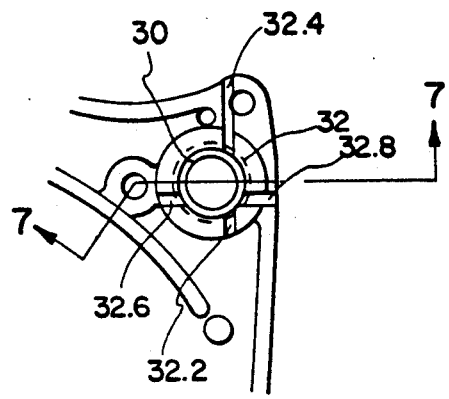
FIG. 6 shows the locking pin portion of FIG. 2.
Figure 7:
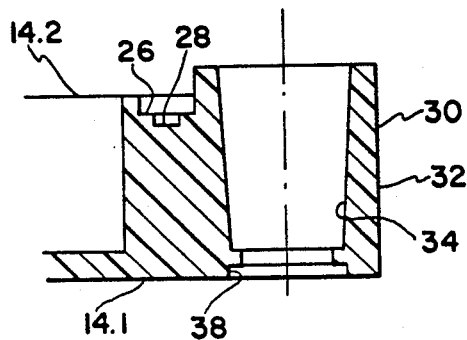
FIG. 7 is a sectional view taken on line 7—7 of FIG. 6.

A strand of floss is trained from a spool 40 shown in dash lines in FIG. 2 and 4 along a path with a first portion indicated by dash line 42, guided around end 14.4 of wall 14.2, through grooves 32.2, slot 22.4, groove 32.4 (see FIG. 6), over to the distal end portion 16 through groove 14.6 in wall 14.2 into the housing and with a second portion of the floss strand indicated by dash line 44, guided around the outside portions of pegs 24 back to locking station 30 through grooves 32.6, slot 22.6 and groove 32.8.

Housing half 14 is formed with an opening 14.8 in wall 14.2 which is adapted to receive a leg of a strand severing means 20 (FIG. 1) as will be explained below.

With particular reference to FIGS. 4 and 5, housing half 12 is shown which essentially is a mirror image of housing half 14. Housing half 12 has a top wall 12.1 (top wall 12.1 is shown as a bottom wall in FIG. 4) and upstanding outer side wall 12.2 and inner side wall 12.4. A plurality of apertures 25 are formed along arm 18 in reinforced bosses 27 and are adapted to receive respective pegs 24 of housing half 14 therein. Apertures 29, spaced around main body portion 15, are adapted to receive respective pegs 28 of housing half 14 therein.

A generally rectangular opening 12 10 is adapted to receive rectangular portion 22.2 of pin 22 to maintain a pre-selected angular orientation of pin 22 as mentioned, supra.

Grooves 32.2, 32.4, 32.6 and 32.8 are formed in the outer portion of side wall 12.2 in alignment with corresponding grooves in hub 32 in housing half 14 along with grooves 12.6 in arm 18 to facilitate guidance of a floss strand along its intended path. Thus, a spool of floss is placed in housing half 14 with the free end of the floss strand guided through the locking station with the first portion of the strand trained through upper slot 22.4, across the open space outside the housing to distal end portion 16, then the second portion of the stand is trained around pegs 24 back through the locking station and through slot 22.6 and back out of the housing. A leg (not shown) of the severing mechanism is placed in space 14.8 and then housing half 12 is placed onto half 14 with the pegs received in their respective apertures locking the severing means to the housing and capturing the floss spool therein.

When the locking pin is in the locked position, both the first and second portions of strand S passing through slots 22.4, 22.6 respectively are pulled down into tight functional engagement between the closely fitting surface portions 22.8 of pin 22 and 34 of the pin seat so that the strand is firmly locked in place around the loop extending from the locking station, along the arcuate arm and back to the locking station. The taught strand extending outside the housing from the main body portion over to the arcuate arm can then be used to floss one's teeth in a conventional manner. When finished, the locking pin can be pushed to the unlocked position with surface portion 22.8 of the pin loosely received in its seat, surface portion 34, the used strang S can be pulled out from the dispenser, the pin pushed to the locked portion and the length severed using severing means 20 and discarded.

Alternatively, the dispenser can be used to provide any selected length of floss by placing the locking pin the unlocked position, pulling out the desired length, reapplying the lock and severing the selected length.

Although the invention has been disclosed herein in its preferred form, those skilled in the art will readily recognize that various changes and modifications may be made thereto without departing from the spirit and scope of the invention as set forth in the claims appended hereto.

I claim:

1. Dental floss dispenser apparatus comprising
a housing having a floss supply section and being formed with an arm having a distal free end portion,
a locking station,
floss guide means for guiding a strand of floss from the supply section with a first portion of floss passing through the locking station to the distal free end portion and with a second portion of floss passing through the locking station and out of the dispenser apparatus,
the locking station comprising a pin in a pin seat, the pin being movable between a locking position and an unlocking position, the pin locking both the first and the second portions of the floss when int he locked position and unlocking both the first and the second portions of the floss when in the unlocked position and means to cause the pin to snap between the locking position and the unlocking position including a protrusion formed on the pin and a ridge formed in the housing and moved past the ridge is moving the pin between the locked and unlocked positions.

2. Dental floss dispenser apparatus according to claim 1 in which the pin and pin seat are each formed with a frusto-conical surface portion and first and second slots are formed in the pin.

3. Dental floss dispenser apparatus according to claim 2 in which the pin has a longitudinal axis and has opposite end portions and the frusto-conical surface portion is disposed intermediate the opposite end portions.

4. Dental floss dispenser apparatus according to claim 3 in which the slots have opposed side walls and a plane extending generally parallel to the side walls lies perpendicular to the longitudinal axis.

5. Dental floss dispenser apparatus according to claim 4 in which the slots are spaced from one another along the longitudinal axis.

6. Dental floss dispenser apparatus according to claim 4 in which the first portion of the floss is guided through the locking station in a first direction in alignment with one of the first and second slots and the second portion is guided through the locking station in a second direction generally perpendicular to the first direction and in alignment with the other of the first and second slots, the slots each having a bottom surface which extends in a direction generally perpendicular to one another.

7. Dental floss dispenser apparatus according to claim 6 further including anti-rotational means to maintain a selected angular orientation of the pin.

8. Dental floss dispenser apparatus according to claim 7 in which the anti-rotational means includes at least one end portion of the pin having a rectangular outer periphery and which is receivable in a corresponding rectangular passageway in the housing.

9. Dental floss dispenser apparatus according to claim 1 in which the arm is generally arcuate in shape and a series of pegs are formed in the arm to form part of the floss guide means.

10. Dental floss dispenser apparatus according to claim 1 in which the housing is formed from the first half adapted to be received in respective apertures formed in the second half, selected pegs additionally serving as part of the floss guide means.

11. Dental floss dispensing apparatus according to claim 1 in which the housing is formed of a moldable synthetic resin.

12. Dental floss dispenser apparatus comprising
a housing having a floss supply section and being formed with an arm having a distal free end portion,
a locking station,
floss guide means for guiding a strang of floss from the supply section with a first portion of floss passing through the locking station in a first direction to the distal free end portion and with a second portion of floss passing through the locking station in a second direction generally perpendicular to the first direction and out of the dispenser apparatus,
the locking station comprising a pin in a pin seat, the pin being movable between a locking position and an unlocking position, first and second floss receiving slots formed in the pin in alignment with the respective first and second directions, the slots each having a bottom surface which extends in a direction generally perpendicular to one another, the pin locking both the first and the second portions of the floss when in the locking position and unlocking both the first and second portions of the floss when in the unlocking position.

* * * * *